(12) United States Patent
Kendall et al.

(10) Patent No.: US 8,061,006 B2
(45) Date of Patent: Nov. 22, 2011

(54) PARTICLE CASSETTE, METHOD AND KIT THEREFOR

(75) Inventors: Mark Anthony Fernance Kendall, Oxford (GB); Edward R. Smith, Oxford (GB); John Watson, Oxford (GB); Graham Ford, Oxford (GB)

(73) Assignee: Powderject Research Limited, Oxford (GB)

( * ) Notice: Subject to any disclaimer, the term of this patent is extended or adjusted under 35 U.S.C. 154(b) by 901 days.

(21) Appl. No.: 10/484,751

(22) PCT Filed: Jul. 25, 2002

(86) PCT No.: PCT/GB02/03395
§ 371 (c)(1),
(2), (4) Date: May 5, 2004

(87) PCT Pub. No.: WO03/011379
PCT Pub. Date: Feb. 13, 2003

(65) Prior Publication Data
US 2004/0255447 A1    Dec. 23, 2004

Related U.S. Application Data

(60) Provisional application No. 60/307,986, filed on Jul. 26, 2001.

(51) Int. Cl.
*B23P 11/02* (2006.01)
*A61M 5/30* (2006.01)

(52) U.S. Cl. ............... 29/450; 29/453; 29/458; 29/469; 29/463; 29/525.01; 604/70; 604/68; 604/72; 222/92; 222/93; 222/94; 222/107; 206/571

(58) Field of Classification Search ............... 29/448, 29/450, 453, 458, 469, 525, 525.01, 463; 604/68, 70, 72, 131, 140; 222/92, 93, 94, 222/107; 206/570, 571, 572, 63.5, 219, 222
See application file for complete search history.

(56) References Cited

U.S. PATENT DOCUMENTS

| 1,300,654 | A |   | 4/1919  | Rose |
|-----------|---|---|---------|------|
| 1,434,460 | A | * | 11/1922 | Tibbatts .............. 220/4.26 |
| 1,774,258 | A |   | 8/1930  | English |

(Continued)

FOREIGN PATENT DOCUMENTS

DE    1 047 385    12/1958

(Continued)

OTHER PUBLICATIONS

James H. Oard, et al, "Transient Gene Expression in Maize, Rice, and Wheat Cells Using an Airgun Apparatus", Plant Physiol (1990) 92, pp. 334-339.

(Continued)

*Primary Examiner* — Essama Omgba
(74) *Attorney, Agent, or Firm* — Foley & Lardner LLP (57) ABSTRACT

A kit of parts for use in the manufacture of a particle cassette for a needleless syringe device. The kit may include a first cassette part having a first rupturable membrane sealed thereto and a second cassette part having a second rupturable membrane sealed thereto. The first and second cassette parts may be arranged to be attachable together so as to create a chamber for the confinement of particles between the first and second membranes. The first and second cassette parts may be substantially annular and the first cassette part defines a receptacle for receiving particles. The second cassette part may be attachable concentrically around or inside the first cassette part.

52 Claims, 8 Drawing Sheets

U.S. PATENT DOCUMENTS

| | | | |
|---|---|---|---|
| 1,861,047 A * | 5/1932 | Colton | 424/10.3 |
| 2,147,158 A | 2/1939 | Goldenthal | |
| 2,151,418 A | 3/1939 | Bolte | |
| 2,307,986 A | 1/1943 | Bolte et al. | |
| 2,314,527 A * | 3/1943 | Taylor | 53/399 |
| 2,470,298 A | 5/1949 | Fields | |
| 2,478,715 A | 8/1949 | Schmitt | |
| 2,594,093 A | 4/1952 | Thompson | |
| 3,216,562 A | 11/1965 | Lockood | |
| 3,324,902 A * | 6/1967 | Lense | 141/1 |
| 3,508,677 A * | 4/1970 | Laibson et. al. | 220/590 |
| 3,659,600 A * | 5/1972 | Merrill | 604/891.1 |
| 3,664,495 A * | 5/1972 | Graham et al. | 220/8 |
| 3,674,028 A | 7/1972 | Ogle | |
| 3,735,761 A * | 5/1973 | Hurschman et al. | 604/88 |
| 3,736,933 A | 6/1973 | Szabo | |
| 3,782,380 A | 1/1974 | Van Der Gaast | |
| 3,788,315 A | 1/1974 | Laurens | |
| 3,797,490 A * | 3/1974 | Hurschman et al. | 604/88 |
| 3,797,491 A * | 3/1974 | Hurschman | 604/511 |
| 3,810,469 A * | 5/1974 | Hurschman | 604/88 |
| 3,967,761 A | 7/1976 | Melton, Jr. et al. | |
| 4,031,892 A | 6/1977 | Hurschman | |
| 4,081,077 A | 3/1978 | Franck | |
| 4,180,173 A * | 12/1979 | Diaz | 215/6 |
| 4,226,236 A | 10/1980 | Genese | |
| 4,360,969 A * | 11/1982 | Collier | 29/881 |
| 4,362,242 A * | 12/1982 | Cheetham | 206/219 |
| 4,416,370 A * | 11/1983 | Beall | 206/217 |
| 4,474,303 A * | 10/1984 | Maccise | 220/4.27 |
| 4,515,586 A | 5/1985 | Mendenhall et al. | |
| 4,517,815 A * | 5/1985 | Basso | 62/457.5 |
| 4,581,875 A * | 4/1986 | MacLaughlin et al. | 53/467 |
| 4,596,556 A | 6/1986 | Morrow et al. | |
| 4,627,432 A | 12/1986 | Newell et al. | |
| 4,703,863 A * | 11/1987 | Kohus | 215/11.1 |
| 4,738,817 A * | 4/1988 | Wittwer et al. | 264/328.14 |
| 4,774,085 A | 9/1988 | Fidler | |
| 4,778,054 A | 10/1988 | Newell et al. | |
| 4,778,068 A * | 10/1988 | Kohus | 215/11.1 |
| 4,811,731 A | 3/1989 | Newell et al. | |
| 4,852,757 A * | 8/1989 | Gold | 220/4.03 |
| 4,858,759 A | 8/1989 | Mauthe et al. | |
| 4,863,017 A | 9/1989 | Vlock | |
| 4,893,721 A * | 1/1990 | Bodenmann et al. | 220/8 |
| 4,910,866 A * | 3/1990 | Allen | 29/827 |
| 4,939,827 A * | 7/1990 | Iizuka | 29/898.054 |
| 4,945,050 A | 7/1990 | Sanford et al. | |
| 4,966,581 A | 10/1990 | Landau | |
| 4,991,377 A * | 2/1991 | Marchesini | 53/478 |
| 5,036,006 A | 7/1991 | Sanford et al. | |
| 5,042,472 A | 8/1991 | Bunin | |
| 5,046,618 A | 9/1991 | Wood | |
| 5,053,389 A | 10/1991 | Balschmidt et al. | |
| 5,062,830 A | 11/1991 | Dunlap | |
| RE33,801 E | 1/1992 | Green | |
| 5,100,792 A | 3/1992 | Sanford et al. | |
| 5,102,388 A | 4/1992 | Richmond | |
| 5,120,657 A | 6/1992 | McCabe et al. | |
| 5,141,496 A | 8/1992 | Dalto et al. | |
| 5,149,655 A | 9/1992 | McCabe et al. | |
| 5,179,022 A | 1/1993 | Sanford et al. | |
| 5,188,615 A | 2/1993 | Haber et al. | |
| 5,204,253 A | 4/1993 | Sanford et al. | |
| 5,207,217 A | 5/1993 | Cocozza et al. | |
| 5,228,573 A * | 7/1993 | Pavelle et al. | 206/459.1 |
| 5,239,991 A | 8/1993 | Chawla et al. | |
| 5,256,142 A | 10/1993 | Colavecchio | |
| 5,349,947 A | 9/1994 | Newhouse et al. | |
| 5,360,410 A | 11/1994 | Wacks | |
| 5,371,015 A | 12/1994 | Sanford et al. | |
| 5,394,980 A | 3/1995 | Tsai | |
| 5,415,162 A | 5/1995 | Casper et al. | |
| 5,422,129 A * | 6/1995 | Draddy | 426/115 |
| 5,474,195 A * | 12/1995 | Pai | 220/4.26 |
| 5,478,744 A | 12/1995 | Sanford et al. | |
| 5,492,112 A | 2/1996 | Mecikalski et al. | |
| 5,533,505 A | 7/1996 | Källstrand et al. | |
| 5,560,490 A | 10/1996 | Chawla | |
| 5,575,281 A | 11/1996 | Mecikalski | |
| 5,584,807 A | 12/1996 | McCabe | |
| 5,630,796 A | 5/1997 | Bellhouse et al. | |
| 5,658,892 A | 8/1997 | Flotte et al. | |
| 5,690,249 A * | 11/1997 | Karlsten | 220/666 |
| 5,833,089 A * | 11/1998 | Manni et al. | 215/249 |
| 5,865,796 A | 2/1999 | McCabe | |
| 5,899,880 A | 5/1999 | Bellhouse et al. | |
| 5,947,928 A | 9/1999 | Muller | |
| 6,003,706 A * | 12/1999 | Rosen | 220/4.26 |
| 6,004,286 A | 12/1999 | Bellhouse et al. | |
| 6,010,478 A | 1/2000 | Bellhouse et al. | |
| 6,013,050 A | 1/2000 | Bellhouse et al. | |
| 6,165,155 A * | 12/2000 | Jacobsen et al. | 604/156 |
| 6,168,587 B1 | 1/2001 | Bellhouse et al. | |
| 6,276,547 B1 * | 8/2001 | Petryna | 220/4.03 |
| 6,475,181 B1 | 11/2002 | Potter et al. | |
| 6,592,545 B1 * | 7/2003 | Bellhouse et al. | 604/69 |
| 6,595,352 B2 * | 7/2003 | Bleuer | 206/63.5 |
| 6,685,669 B2 * | 2/2004 | Bellhouse et al. | 604/68 |
| 6,881,200 B2 * | 4/2005 | Bellhouse et al. | 604/68 |
| 6,923,800 B2 * | 8/2005 | Chen et al. | 604/892.1 |
| 6,929,005 B2 * | 8/2005 | Sullivan et al. | 128/203.21 |
| 6,949,154 B2 * | 9/2005 | Hochrainer et al. | 156/69 |
| 6,953,039 B2 * | 10/2005 | Scarrott et al. | 128/200.14 |
| 6,966,899 B2 * | 11/2005 | Hochman et al. | 604/198 |
| 7,014,651 B2 * | 3/2006 | Worthen et al. | 607/105 |
| 7,044,134 B2 * | 5/2006 | Khairkhahan et al. | 128/887 |
| 7,121,402 B2 * | 10/2006 | Van Heerden et al. | 206/222 |
| 7,562,771 B2 | 7/2009 | Fontana | |
| 7,614,496 B2 | 11/2009 | Dvorak et al. | |
| 7,618,394 B2 * | 11/2009 | Bellhouse et al. | 604/70 |
| 7,691,407 B2 * | 4/2010 | Clarke et al. | 424/453 |
| 7,942,846 B2 * | 5/2011 | Bellhouse et al. | 604/70 |
| 2001/0015326 A1 * | 8/2001 | Bleuer | 206/63.5 |
| 2002/0091353 A1 * | 7/2002 | Bellhouse et al. | 604/68 |
| 2003/0019558 A1 * | 1/2003 | Smith et al. | 156/61 |
| 2004/0158197 A1 * | 8/2004 | Bellhouse et al. | 604/70 |
| 2005/0010168 A1 * | 1/2005 | Kendall | 604/70 |
| 2006/0272963 A1 * | 12/2006 | Sharon | 206/219 |
| 2006/0289316 A1 * | 12/2006 | Henry | 206/219 |
| 2007/0185450 A1 * | 8/2007 | De Polo et al. | 604/131 |
| 2009/0110723 A1 * | 4/2009 | McAllister | 424/454 |
| 2010/0298767 A1 * | 11/2010 | Bates et al. | 604/72 |

FOREIGN PATENT DOCUMENTS

| | | |
|---|---|---|
| EP | 0 313 992 | 5/1989 |
| EP | 0 371 838 | 6/1990 |
| EP | 0 406 778 | 1/1991 |
| EP | 0 458 641 | 11/1991 |
| EP | 0 469 814 | 2/1992 |
| EP | 0 734 737 | 10/1996 |
| EP | 0 776 224 | 6/1997 |
| EP | 0 951 917 A2 | 10/1999 |
| FR | 2 360 031 | 12/1978 |
| GB | 501 564 | 3/1939 |
| GB | 677 523 | 8/1952 |
| GB | 2 206 794 | 1/1989 |
| JP | 50-101521 | 8/1975 |
| WO | WO 91/18991 | 12/1991 |
| WO | WO 92/04439 | 3/1992 |
| WO | WO 92/10225 | 6/1992 |
| WO | WO 92/12799 | 8/1992 |
| WO | WO 93/03779 | 3/1993 |
| WO | WO 95/19799 | 7/1995 |
| WO | WO 99/01168 | 1/1999 |
| WO | WO 99/01169 | 1/1999 |
| WO | WO 00/44421 | 8/2000 |
| WO | WO 00/62846 | 10/2000 |
| WO | WO 01/05455 | 1/2001 |
| WO | WO 02/07803 | 1/2002 |
| WO | WO 02/055139 | 7/2002 |
| WO | WO 2007141501 A2 * | 12/2007 |

OTHER PUBLICATIONS

R. Sanders Williams, et al, "Introduction of foreign genes into tissues of living mice by DNA-coated microprojectiles", Genetics (1991), pp. 2726-2730.

The Notice of References in the Corresponding U.S. Appl. No. 12/071,324, dated Dec. 27, 2010.

* cited by examiner

SECTION A-A

Fig. 15

PARTICLE CASSETTE, METHOD AND KIT THEREFOR

TECHNICAL FIELD OF THE INVENTION

The present invention relates generally to the retention of particles prior to the needleless injection of those particles in a gas stream. More specifically, the present invention relates to particle cassettes having a pair of membranes which retain the particles in a chamber therebetween.

BACKGROUND TO THE INVENTION

Needleless syringe devices are known from WO 94/24263. In this document, a needleless syringe is disclosed which entrains particles in a gas stream accelerated through a nozzle so that the particles may be injected into a target, such as human skin or other cells. For many applications, there is a need for the particles to be maintained in a sterile environment prior to actuation of the device. WO 94/24263 discloses for this purpose a particle cassette comprising a central annular ring having rupturable diaphragms sealed to each face so as to form a self contained sealed unit containing the particles to be injected. Upon actuation of the device, the diaphragms rupture allowing the particles initially contained between the diaphragms to be entrained in the gas flow and then delivered into the target.

SUMMARY OF THE INVENTION

FIGS. 1*a* to 1*d* of the accompanying schematic drawings show steps in the manufacture of the particle cassette disclosed WO 94/24263. A substantially annular ring (10) is shown in axi-symmetric cross-section in FIG. 1*a*. The ring has an open central section defining a chamber (11). In a first step of the manufacturing process a rupturable diaphragm (12) is sealed to the bottom face of the annular ring (10). This results in the construction shown in FIG. 1*b*. Then, as shown in FIG. 1*c*, particles (13) are supplied to the chamber (11). The particles (13) so supplied are those to be injected into the target. The last stage in manufacture comprises sealing a second membrane (14) onto the other face of the annular ring so as to seal the particles (13) within the central chamber (11). The cassette can then be handled while the particles are maintained in a sterile environment.

An exemplary needleless syringe is shown in FIG. 15. As can be seen, the needleless syringe comprises a reservoir (100) of compressed gas connected to a valve (110). Downstream of the valve is an expansion chamber (120) the particle cassette (30) and a nozzle section (140). As shown in FIG. 15 the nozzle section (140) comprises an upstream convergent portion (150) downstream of which is a throat (160) followed by a divergent portion (170). To activate the syringe, the valve (110) is actuated and gaseous pressure flows from the reservoir (100) into the expansion chamber (120). Pressure builds up behind the upstream membrane (12) until it reaches a sufficient value to cause the upstream membrane (12) to burst. The gas thereafter entrains the particles and the pressure once again builds up behind downstream membrane (14). Shortly afterwards, the downstream membrane (14) bursts so that the gas (with the particles (13) entrained) can be accelerated in the nozzle (140) and thence into a target (180).

WO 94/24263 discloses that the diaphragm should preferably be heat sealed to the faces of the annular ring. Heat sealing has been found to be a particularly easy and repeatable method of sealing the diaphragms to the ring of the cassette body.

It has been found that the above-mentioned configuration has a disadvantage associated with its manufacture, which may become especially deleterious when heat-sensitive particles (e.g. powdered drugs) are to be carried by the cassette. After the particles have been supplied to the chamber (11) formed by the annular ring (10) and the bottom membrane (12), the heat sealing of the top membrane (14) onto the ring (10) can sometimes result in a degradation of the particles. This degradation may take the form of melting, causing particle deformation, particle agglomeration and other undesirable physical and chemical changes in the product. Further, the melt may affect the therapeutic effect of the particles.

Accordingly, the present invention seeks to alleviate this problem by providing a particle cassette, a kit of parts and a method for the manufacture therefor in which the possibility of the particles melting during manufacture is much reduced.

In accordance with the first aspect of the present invention, there is provided a kit of parts for use in the manufacture of a particle cassette for a needleless syringe device, said kit comprising:

- a first cassette part having a first rupturable membrane sealed thereto; and
- a second cassette part having a second rupturable membrane sealed thereto; said first and second cassette parts being arranged to be attachable together so as to create a chamber for the confinement of particles between said first and second membranes.

Thus, since the membranes are sealed to first and second cassette parts (possibly by heat sealing) before the particles are supplied to either of the cassette parts, there is a much reduced possibility of the membrane heat sealing process influencing the particle condition or composition. Further, the invention provides a quick and easy method of manufacturing a particle cassette and has these advantages over processes which do not involve heat sealing.

Preferably, the first and second cassette parts are annular such that the second part is attachable concentrically around or inside the first cassette part. This allows the first cassette part to extend substantially along the whole width of the particle cassette making it easier to fill the first part with particles prior to attaching the second part.

To attach the first and second parts together, a variety of mechanisms may be used, including interference fits, friction fits, screw fits, detents and recesses, close tolerances, gluing etc. A snap fit may be provided for by arranging corresponding features on each of the first and second parts (for example a detent and a recess).

In order to ensure a consistent width of particle cassette, it is preferable to provide a seating face on each of the first and second parts, such a seating face providing a minimum possible width of particle cassette when assembled.

A tapered face on each of the first and second parts allows the parts to be brought together easily during assembly.

A third cassette part may be used to attach the first and second parts together. In a preferred embodiment, the third cassette part is inserted in an annular apace between the first and second cassette parts, to provide a secure attachment (or “locling”). The third part preferably has a third membrane to ensure sterility and may be provided with one or more protrusions to ensure an interference fit with the second cassette part.

In a second aspect of the invention, there is provided a particle cassette for a needleless syringe comprising an assembled kit according to the first aspect and particles provided in the chamber between the first and second membranes.

According to a third aspect of the present invention, there is provided a needleless syringe including the particle cassette of the second aspect of the invention.

According to a fourth aspect of the invention, there is provided a method of assembling a particle cassette for a needleless syringe device, said method comprising:
(a) sealing a first rupturable membrane to a first cassette part;
(b) sealing a second rupturable membrane to a second cassette part;
(c) applying particles to said first cassette part;
(d) attaching said first and second cassette parts together so as to create a chamber confining said supplied particles between said first and second membranes.

The sealing of the membranes to the cassette parts independently from the steps of supplying particles to one of the cassette parts and attaching the cassette parts together ensures that the method used for sealing the membranes to the cassette parts does not unduly influence the quality of the particles in the cassette.

Preferably, attaching step (d) does not involve the application of any heat at all and it is preferably carried out at the same temperature as supplying step (c) to ensure that the particles are not affected by the step of attaching the first and second cassette parts together.

It is not essential that supplying step (c) is carried out after sealing step (b) since the second membrane may be sealed to the second cassette part after the particles have been supplied to the first cassette part.

BRIEF DESCRIPTION OF THE DRAWINGS

Embodiments of the present invention will now be described, by way of example only, with reference to the accompanying schematic drawings, in which.

DESCRIPTION OF PREFERRED EMBODIMENTS

In the drawings the components are not drawn to scale. The drawings are schematic for reasons of clarity. In reality the thickness of the rupturable diaphragms may be much less than that shown and/or the volume of particles may be so small as barely to be visible to the naked eye.

The present invention avoids the possibility of the heat sealing of the membranes affecting the particle quality by ensuring that the particles are confined within the chamber of the cassette by a step other than one involving heat sealing of one of the membranes. Thus, generally speaking, each of the embodiments of the present invention comprises a first cassette part (20) having a first membrane (22) sealed to a face and a second cassette part (21) having a second membrane (23) sealed to a face. Particles (24) are dispensed into the first cassette part and the second cassette part is then attached. The attachment step should not involve the application of an amount of heat such as is likely to damage the particles. However, heat sealing can be used in the attachment step if the heat is used such that the particles are not likely to be damaged.

Figure 1A:
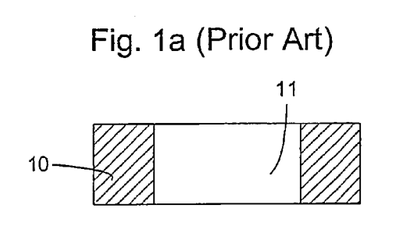
FIGS. 1a to 1d are cross-sectional views showing stages in the manufacture of a particle cassette according to the prior art.
Figure 1B:
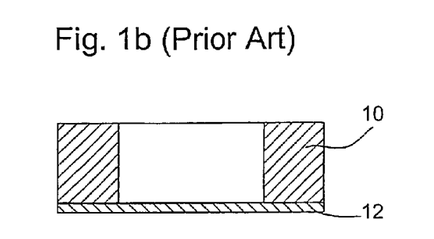
Figure 1C:
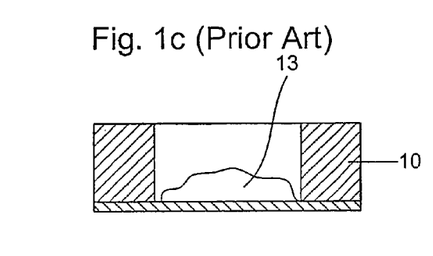
Figure 1D:
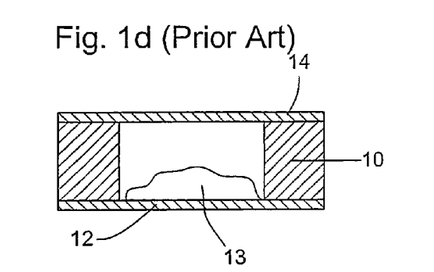
Figure 2A:
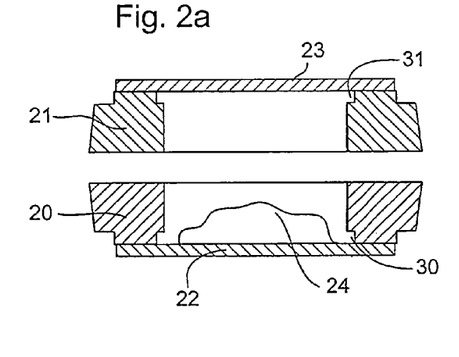
FIGS. 2a and 2b are cross-sectional views showing stages in the manufacture of a particle cassette according to a first embodiment of the invention.
Figure 2B:
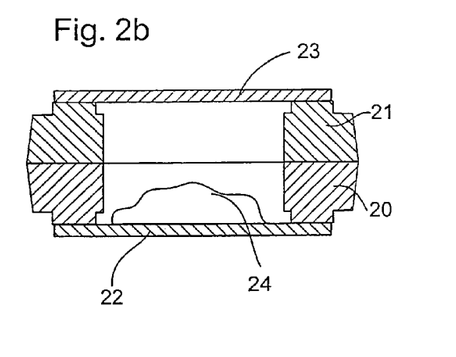

FIGS. 2a and 2b show an axi-symmetric cross-section of the particle cassette according to the first embodiment of the present invention.

In the first embodiment, the first cassette part (20) comprises an annular ring having a first face (the upper face in FIG. 2a) for attachment to a second cassette part (21), the other side of the annular ring having had a first membrane (22) sealed thereto. The second cassette part (21) is substantially identical to the first cassette part, having had a second membrane (23) sealed thereto. The first and second cassette parts, having the first and second membranes respectively, form a kit of parts for use in the manufacture of the particle cassette. The membranes are sealed to the external faces of the respective cassette parts. If heat sealing is used to attach the membranes then a recess (30,31) as shown in FIG. 2a is useful because it allows for some plastic deformation as will be caused by heat sealing in general. In particular, the heat causes local expansion of the cassette material and the recesses (30,31) allow the cassette material to expand without affecting the designed gas flow path (eg by restricting the diameter of the flow path).

In order to manufacture the particle cassette, particles (24) are dispensed to the first cassette part (20) and the first (20) and second (21) cassette parts are attached together so as to create a closed chamber for the confinement of the particles (24) between the first (22) and second (23) membranes. The assembled particle cassette is shown in FIG. 2b.

In use, the particle cassette is located in a needleless syringe device which may have the general construction, and method of operation, described in WO 94/24263 or WO 01/05455, the contents of which are hereby incorporated by way of reference. When located in the syringe device the device construction is advantageously such as to prevent the first cassette part (20) coming away from the second cassette part (21). However, in order to mitigate against further such detachment, the second cassette part (21) may be adhered to the first cassette part (20), for example by gluing or by taping around the external circumference of the particle cassette. This provides a sealed unit of particles which can be handled outside of the needleless syringe device with reduced possibility of particles escaping from between the two cassette halves.

Figure 3:
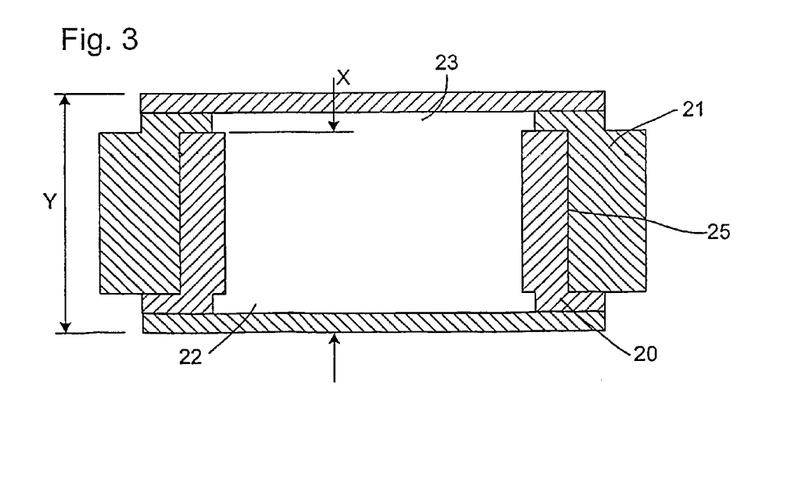
FIG. 3 is a cross-sectional view showing an assembled particle cassette according to a second embodiment of the present invention.

A second embodiment of the invention is shown in FIG. 3. The particles (24) are omitted from inside the particle cassette for the sake of clarity. Further, it is to be noted that the particle cassette shown in FIG. 3 (and those shown in FIGS. 4 to 6 as well) will, prior to assembly, make up a kit of parts according to the first aspect of the present invention.

In the second embodiment, the first cassette part (20) is constituted by a substantially annular member which extends to a height X nearly equal to the height Y of the assembled particle cassette. This greatly facilitates the filling of the first cassette part (21) with particles (24) since a larger receptacle than is provided in the first embodiment can be used to receive particles (24). A further advantage is that the whole internal volume of the cassette can be used to hold particles. In contrast, the first embodiment can only be half filled with particles since the first cassette part (20) has a height equivalent only to approximately half the final height of the cassette.

The second cassette part (21) also has a substantially annular construction and is arranged to be attachable concentrically around the first cassette part (20). If necessary, adhesive can be used at the interface (25) to ensure that the first and second cassette parts do not detatch easily. More preferred, however, is that the cassette parts are attached by an interference fit, whereby the outer diameter of the engaging region of the first cassette part is slightly larger than the inner diameter of the engaging region of the second cassette part (21). In this way, the parts will naturally lock together due to the elastic strain established in each of the first and second cassette parts when the second part (21) is placed around the first part (20).

The second embodiment shown above has advantages over the first embodiment because it does not necessarily require an extra adhesive to be used (an interference fit is instead used) and because the first cassette part defines a larger receptacle area for receiving the particles (24). However, the second embodiment has the disadvantage that it may be difficult or fiddly to assemble, even if one or both of the engaging inner face of the second cassette part and the engaging outer face of the first cassette part is provided with a lead in taper to aid assembly. To overcome this problem, a cassette according to the third embodiment of the invention is provided. Such a cassette is shown in FIG. 4.

Figure 4:
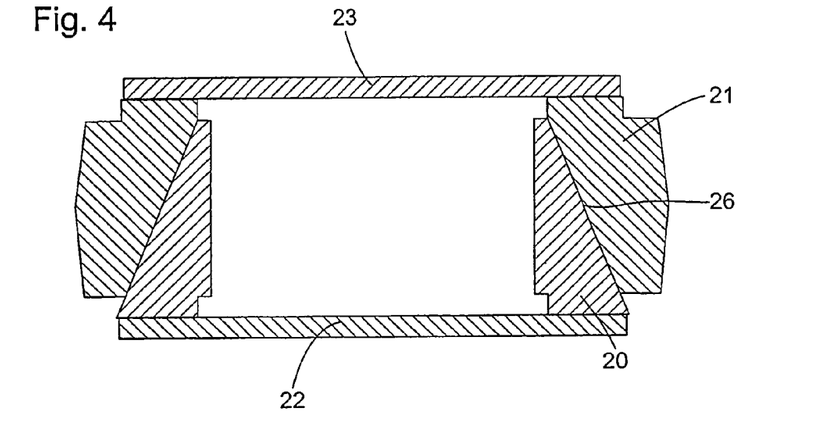
FIG. 4 is a cross-sectional view showing an assembled particle cassette according to a third embodiment of the present invention.

In the third embodiment of the present invention, the outer engaging face of the first cassette part (20) and the inner engaging face of the second cassette part (21) (the interface of which is denoted as (26) in FIG. 4) are tapered so as to allow the second cassette part (21) to be easily placed over the first cassette part (20). Again, although gluing may be used to attach the parts, it is preferable that the first cassette part (20) has a larger outer diameter than the inner diameter of the second cassette part (21) at each point along the height of the cassette. This means that as the parts are brought close to the assembled position shown in FIG. 4, some elastic strain is established in the parts to provide a snug fit. The parts are prevented from coming apart by friction along the tapered interface (26).

The third embodiment of the invention thus has the advantage that it is easier to assemble the kit of parts than the second embodiment of the invention. However, it has the potential disadvantage that the width of the cassette (ie the vertical dimension in FIG. 4) may not necessarily be predicted before the parts are assembled. Depending on the force used to push the first (20) and second (21) cassette parts together, the width may vary over a certain range. For example, if the parts are pressed together very strongly, the width is likely to be less than if the parts are only lightly pressed together. Furthermore, the leading edge of the first cassette part (20) may damage the seal between the second membrane (23) and the second cassette part (21) if the two parts are pushed together too strongly.

To overcome this problem, a particle cassette as shown in the fourth embodiment of the invention is provided.

Figure 5:
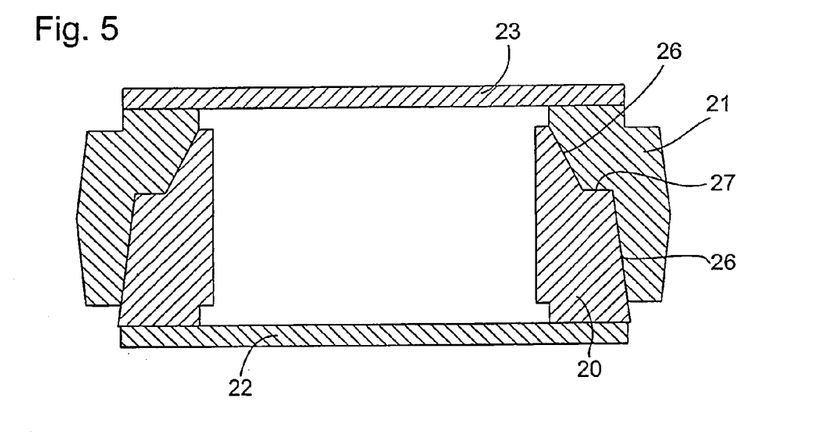
FIG. 5 is a cross-sectional view showing an assembled particle cassette according to a fourth embodiment of the present invention.

In this embodiment, a seating face (27) is provided to each of the first (20) and second (21) cassette parts. As is shown in FIG. 5, once the cassette parts have been pushed together a certain amount, the seating face (27) prevents further movement in the cassette height direction (i.e. the vertical direction in FIG. 5). The fourth embodiment of the invention therefore allows the width dimension of the assembled particle cassette to be reliably ensured. The tapered sections (26) perform the same function as in the third embodiment and the outer surfaces of the first cassette part (20) may again be made to have a slightly larger diameter than the inner surfaces of the second cassette part (21) so as to provide an interference fit. The steeper angle of the lower tapered section 26 provides for a better locked fit. The fairly uniform cross-section in the vicinity of the membranes allows for good heat dissipation during the heat sealing process, if used.

Figure 6:
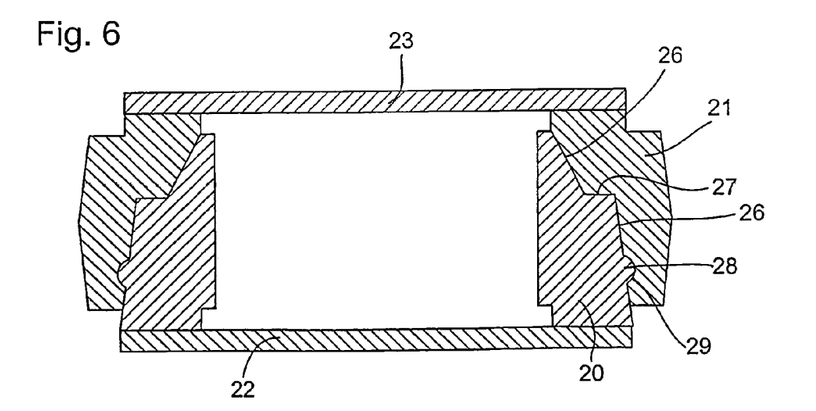
FIG. 6 is a cross-sectional view showing an assembled particle cassette according to a fifth embodiment of the present invention.

While an interference fit is suitable for a lot of purposes, it is often preferable that no elastic strains are built up in the first and second cassette parts, especially if they are to be re-used a lot of times. The fifth embodiment of the invention addresses this problem. FIG. 6 shows an axi-symmetric cross-sectional view of the fifth embodiment of the invention having parts generally similar to those shown in FIG. 5.

The main difference is the provision on each of the first (20) and second (21) cassette parts of corresponding features (28, 29) which provide for a snap fit when the first and second cassette parts are brought together. In particular, the first cassette part (20) comprises a detent (28) located on one of external tapered surfaces (26). Correspondingly, the second cassette part (21) comprises a recess (29) on its respective tapered surface (26). Thus, when the first and second cassette parts are brought together, the detent (28) locates in the recess (29) to lock the two pieces together. During this attaching step, both the first and second cassette parts undergo a momentary elastic strain as the detent (28) engages in the recess (29) but, once assembled, the cassette part can be arranged so that there is little residual strain present. This means that there is no requirement to rely on an interference fit alone to maintain the first and second cassette parts in attachment. The provision of corresponding features also makes it more difficult for the first and second parts to be accidentally detached, providing a stronger lock between the first and second cassette parts and thus a more secure sealed environment for the particles. This is particularly useful when the cassette is to be subject to vibrations, such as those experienced during transportation. The fifth embodiment shown in FIG. 6 is considered to be the best mode of carrying out the invention.

The fifth embodiment has a further advantage in that it provides an assembly that is tamper evident. Once assembled, it is very difficult to prise the cassette parts apart due to the taper lock and detent arrangement. Thus, the assembly could only be opened by destroying one of the membranes or using a very sharp tool to lever apart the parts, which in practice causes obvious deformation of the cassette parts.

FIGS. 7 to 12 show a sixth embodiment of the invention. Unlike the previous embodiments, the particle cassette of the sixth embodiment has three main component parts rather than two.

Figure 7:
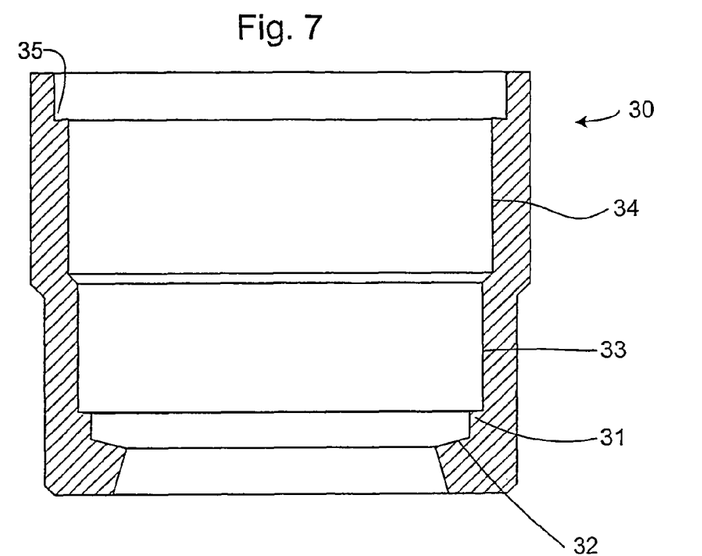
FIG. 7 is a cross-sectional view of a second cassette part according to a sixth embodiment of the present invention.
Figure 8:
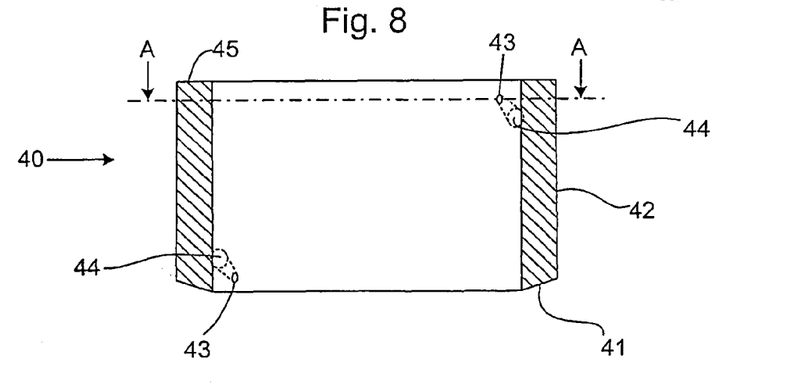
FIG. 8 is a cross-sectional view of a first cassette part according to a sixth embodiment of the present invention.
Figure 9:
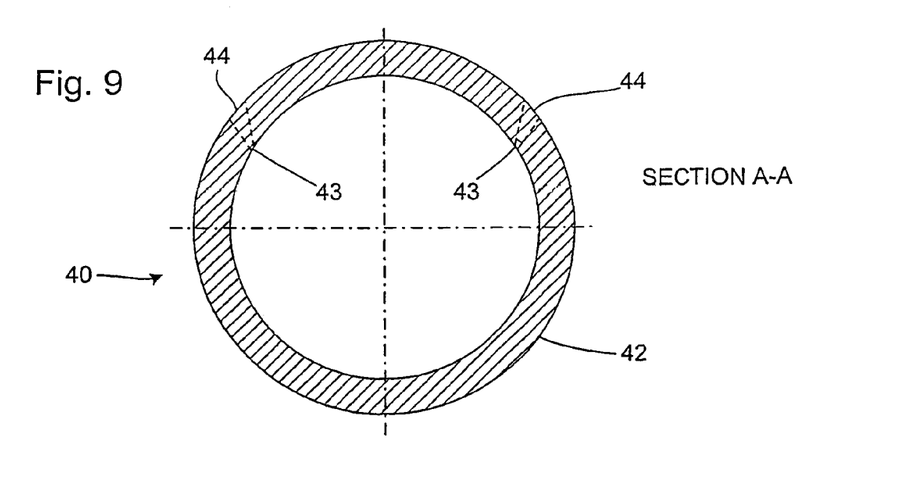
FIG. 9 is a cross-sectional view along the line A-A shown in FIG. 8.

FIGS. 7 and 8 show in cross-sectional view second and first cassette parts respectively. The second cassette part (30) of FIG. 7 is generally cylindrical in configuration having substantially vertical inside walls (33) and (34). The inside wall (33) has a slightly smaller diameter than inside wall (34) for reasons that will become apparent later. A shoulder portion (31) is provided adjacent a seating face (32). The shoulder portion (31) is designed to interact with the external surface of the first cassette part (40), described hereafter. A recess (35) is provided at the top end of the second cassette part (30) and this recess (35) aids in assembling the cassette.

Figure 11:
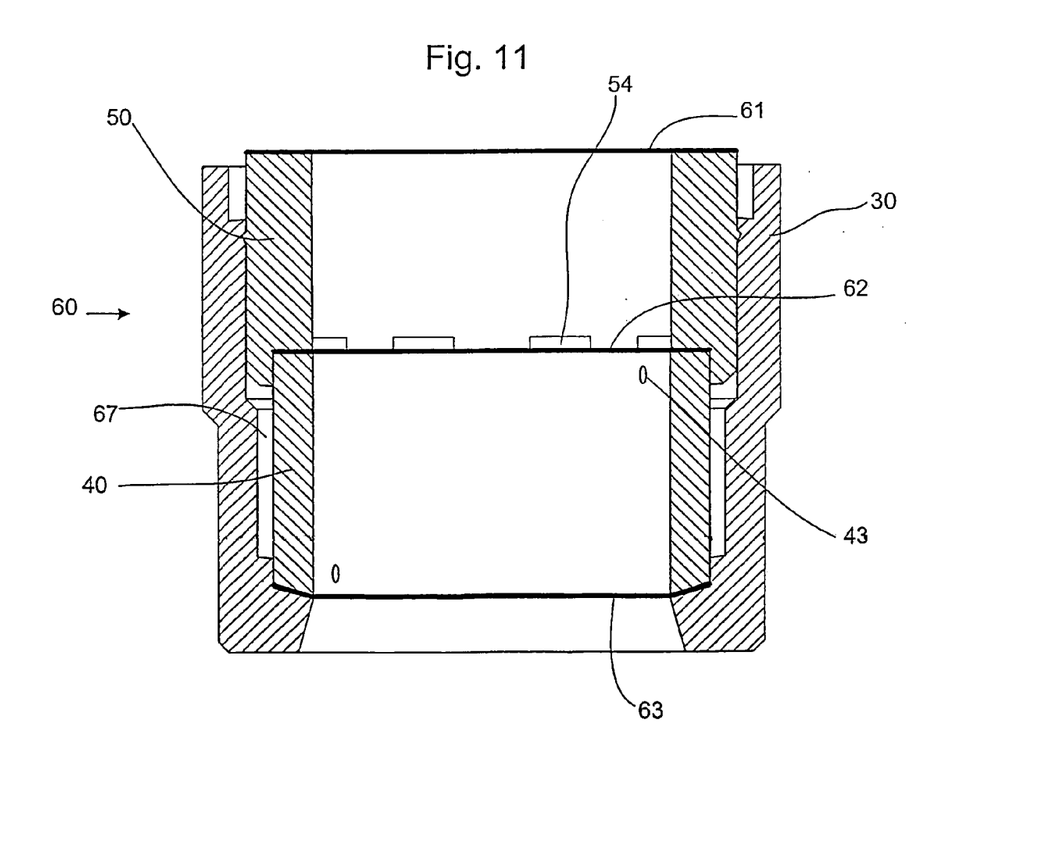
FIG. 11 is a cross-sectional view of an assembled particle cassette according to a sixth embodiment of the present invention.

FIG. 8 shows a first cassette part (40) according to the sixth embodiment of the present invention. The first cassette part (40) comprises a substantially annular member defining within its confines a receptacle for receiving particles. The first cassette part (40) has generally cylindrical outer walls (42) and a slightly tapered seating face (41) at its bottom end. The seating face (41) is intended to rest against the seating face (32) of the second cassette part (30) during use. Furthermore, the shoulder (31) of the second cassette part (30) is intended to abut the outer surface (42) of the first cassette part to provide an interference fit. This configuration is shown in FIG. 11.

Figure 12:
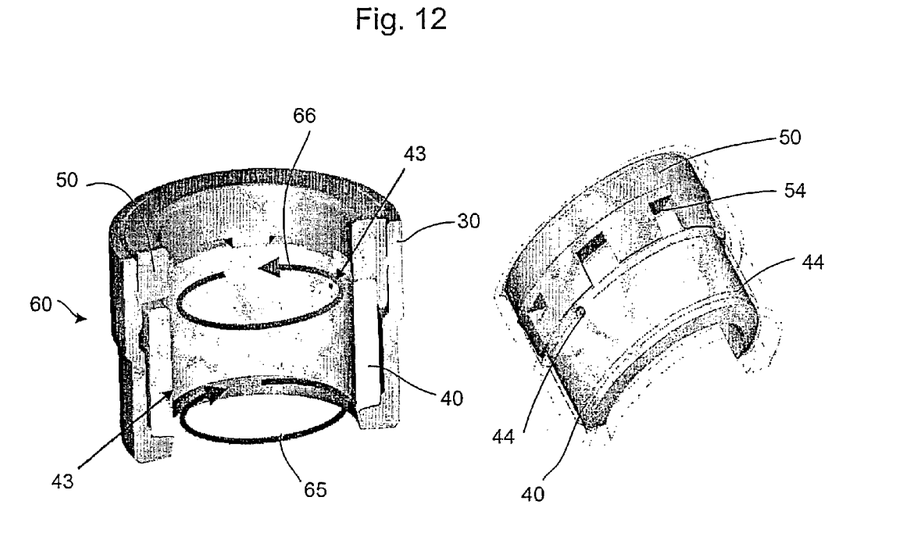
FIG. 12 shows two perspective views of a partially cutaway particle cassette according to the sixth embodiment of the present invention.

Referring back to FIGS. 8 and 9, there are openings (43) on the inner surface of the first cassette part (40) and openings (44) on the outer surface of the first cassette part (40). These openings are connected by transfer ducts such that gas surrounding the first cassette part (40) may enter the receptacle for receiving particles. The transfer ducts are substantially conical and are angled in three dimensions such that when gas flows therethrough a sonic jet is formed which tends to create a swirling gas movement inside the chamber confining the particles. The transfer ducts are angled such that the gas tends to impinge against the membranes located at either side of the first cassette part (40). Furthermore, the holes (43) are provided at different longitudinal ends of the first cassette part (40) and are directed in different directions such that a clockwise gas flow is established at one end of the particle confinement chamber and an anti-clockwise gas flow is established at the other end of the particle confinement chamber. This is illustrated in FIG. 12 wherein the gas flows are referenced (65) and (66). As is clear from FIG. 9, the transfer ducts are provided on the same lateral side of the first cassette part (i.e. above the centre line shown in FIG. 9), and this has been found to provide for good fluidization of the particles when gas pressure is introduced to the openings (44) and a flow of gas is established through the transfer ducts. However, other configurations of transfer duct in the side walls of the first particle cassette part (40) can provide good results and it is not generally essential for the present invention that the transfer ducts have the specific form shown in FIGS. 8 and 9.

Figure 10:
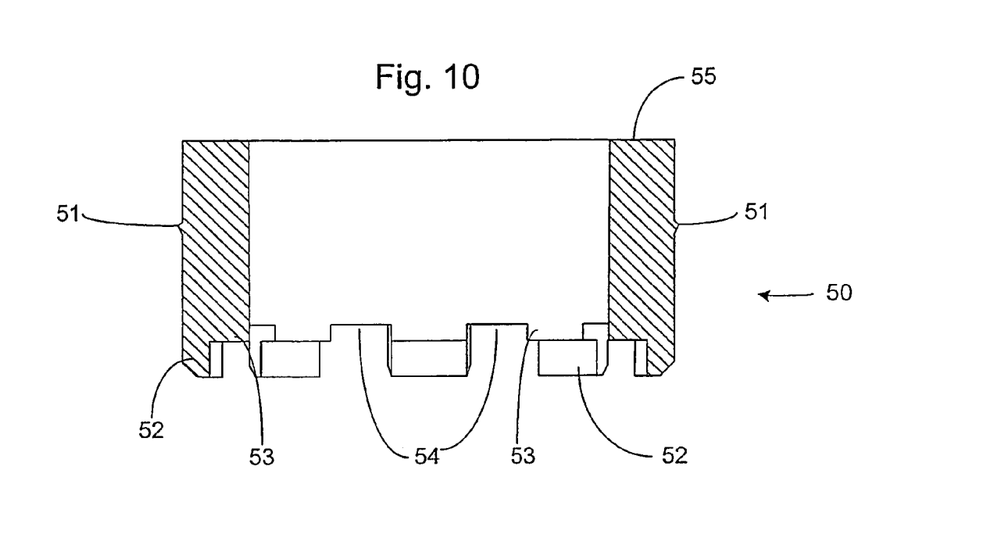
FIG. 10 is a cross-sectional view of a third cassette part according to a sixth embodiment of the present invention.

FIG. 10 shows a third particle cassette part in accordance with the sixth embodiment of the present invention.

The third cassette part (50), in common with the first and second cassette parts, has generally cylindrical inner and outer walls forming an annular-shaped member. One or more protrusions (51) may be formed on the outer walls and these are intended to provide an interference fit against the inner wall (34) of the second cassette part (30), when the particle cassette is assembled. The lower end of the third cassette part (50) has a number of formations (52) around the circumference. The formations (52) are stepped and are designed such that the top part (53) of the formations (52) abuts the top surface of the first cassette part (40) when assembled, as shown in FIG. 11. The formations are spaced apart by vent holes (54) that are formed such that gas may pass through the vent holes (54) when the first and third cassette parts are attached together. The formations (52) are shaped so as to grip, by means of friction, or interference, the top part of the first cassette part (40).

The particle cassette according to the sixth embodiment of the invention takes the form shown in FIG. 11 when assembled. In this embodiment, there are three membranes (61, 62, 63) of which one membrane (61) is relatively thin with a fairly low bursting pressure and is designed to keep the unit sterile in use.

To assemble the particle cassette of the sixth embodiment, a first membrane (62) is heat sealed or bonded to the upper edge of the first cassette part (40). Similarly, the second membranes (63) is heat sealed or bonded to the seating face (32) of the second cassette part (30). The third membrane (61) is heat sealed or bonded to the upper face of the third cassette part (50). The first membrane and first cassette part thus define a receptacle in which the particles may be contained. The openings (43) are very small such that it is very difficult for the particles to pass out of the chamber once inside. Once the particles have been supplied to the chamber of the first cassette part (40), the first cassette part (40) is brought together with the second cassette part (30) with the leading edge of the first cassette part engaging the shoulders (31) of the second cassette part. The first cassette part (40) is pushed home until the seating face (41) of the first cassette part abuts the seating face (32) of the second cassette part (with the second membrane (63) between the two seating faces). In this configuration, the particles are trapped between the first and second membranes. The third cassette part (50) having the third membrane (61) thereon is then pushed in so that the formations (52) slide into the annular gap created between the first and second cassette parts. Interference and/or friction ensure that this movement firmly secures the first and second parts together and effectively "locks" the cassette. It will be appreciated that it is quite difficult to remove the third cassette part once it is installed, especially if the top face (55) of the third cassette part is dimensioned so as to be flush with the top face of the second cassette part when assembled (this is not shown in FIG. 11 however).

The membrane (61) ensures that the particles inside the cassette may not come into contact with any external particles or gases and thus the membrane (61) ensures the sterility of the cassette.

In use, the cassette is inserted into a needleless syringe and gas pressure is supplied to the third membrane (61). The membrane (61) bursts quite easily and gas enters the internal space defined by the third cassette part. Gas is able to flow through the vents (54) and into the annular space (67) between the first cassette part and the second cassette part. From there, gas may pass through the transfer ducts and out through the openings (43) into the particle containment chamber. The jets of gas so formed cause the particles to be fluidized and mixed. Following that, the upstream membrane (62) bursts and the particles are entrained in the bulk of the gas flow followed by the bursting of the downstream membrane (63) shortly thereafter. In this way, the particle cassette of the sixth embodiment provides for pre-mixing and fluidizing of the particles whilst still overcoming the problem that heat sealing of membranes can damage particles when a single piece cassette is used.

The concepts described in relation to the first to fifth embodiments may also be applied to the sixth embodiment in the same way. For example, a snap fit may be provided for if detents and corresponding recesses are provided on either the first and second, first and third or second and third cassette parts respectively.

Heat sealing or adhesive is not necessary in the sixth embodiment and the first and second membranes may be sealed against the first and second cassette parts respectively due to the tight fit between the various cassette parts. For example, the first membrane (62) may be sealed by virtue of being trapped between the first and third cassette parts. Similarly, the second membrane (63) may be trapped between the first and second cassette parts, with no special heat sealing or adhesive step being required.

Figure 15:
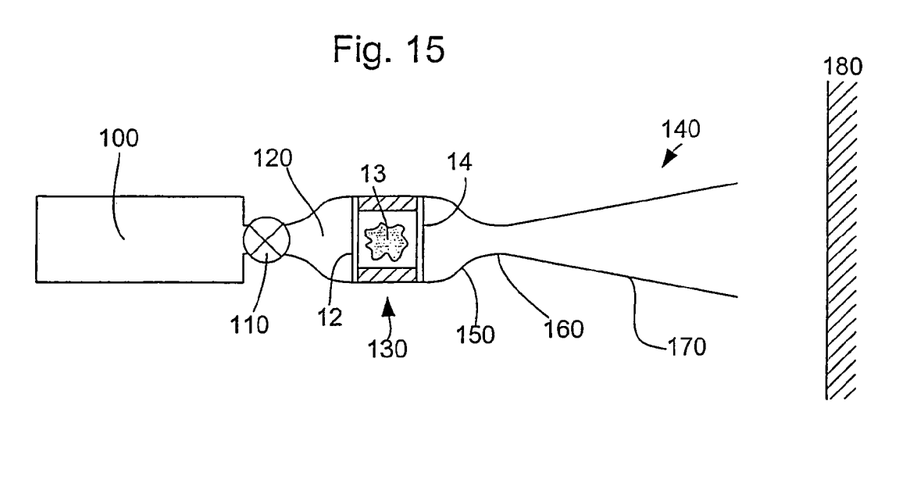
FIG. 15 is a longitudinal cross-sectional view through a needleless syringe which may comprise the particle cassette of any one of the embodiments of the present invention.

As can be seen from FIG. 15 in particular, the first to sixth embodiments are usually used in a configuration such that the particle cassette is located downstream of an expansion chamber (120) in the needleless syringe. The syringe is therefore complex to assemble.

Figure 13:
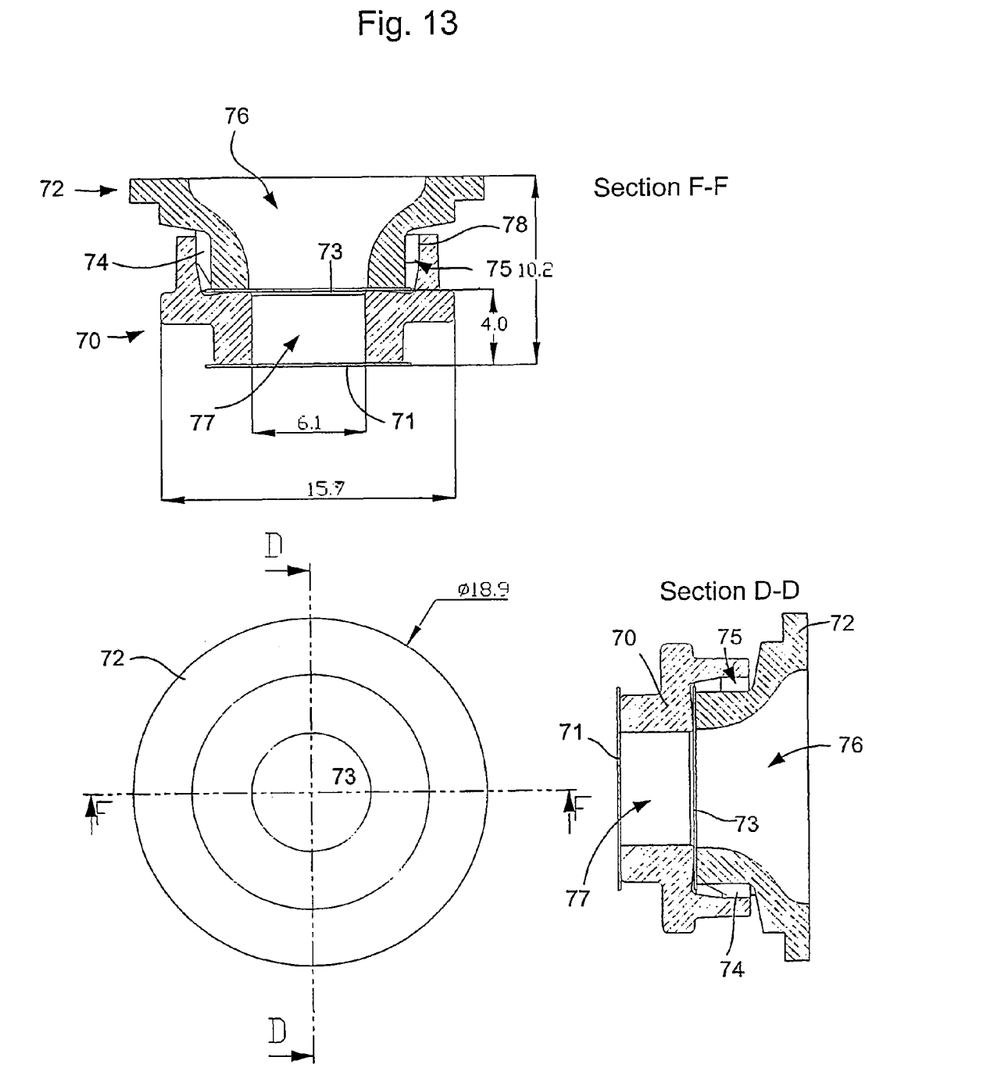
FIG. 13 is a set of three orthographic views of an assembled particle cassette according to a seventh embodiment of the present invention.
Figure 14:
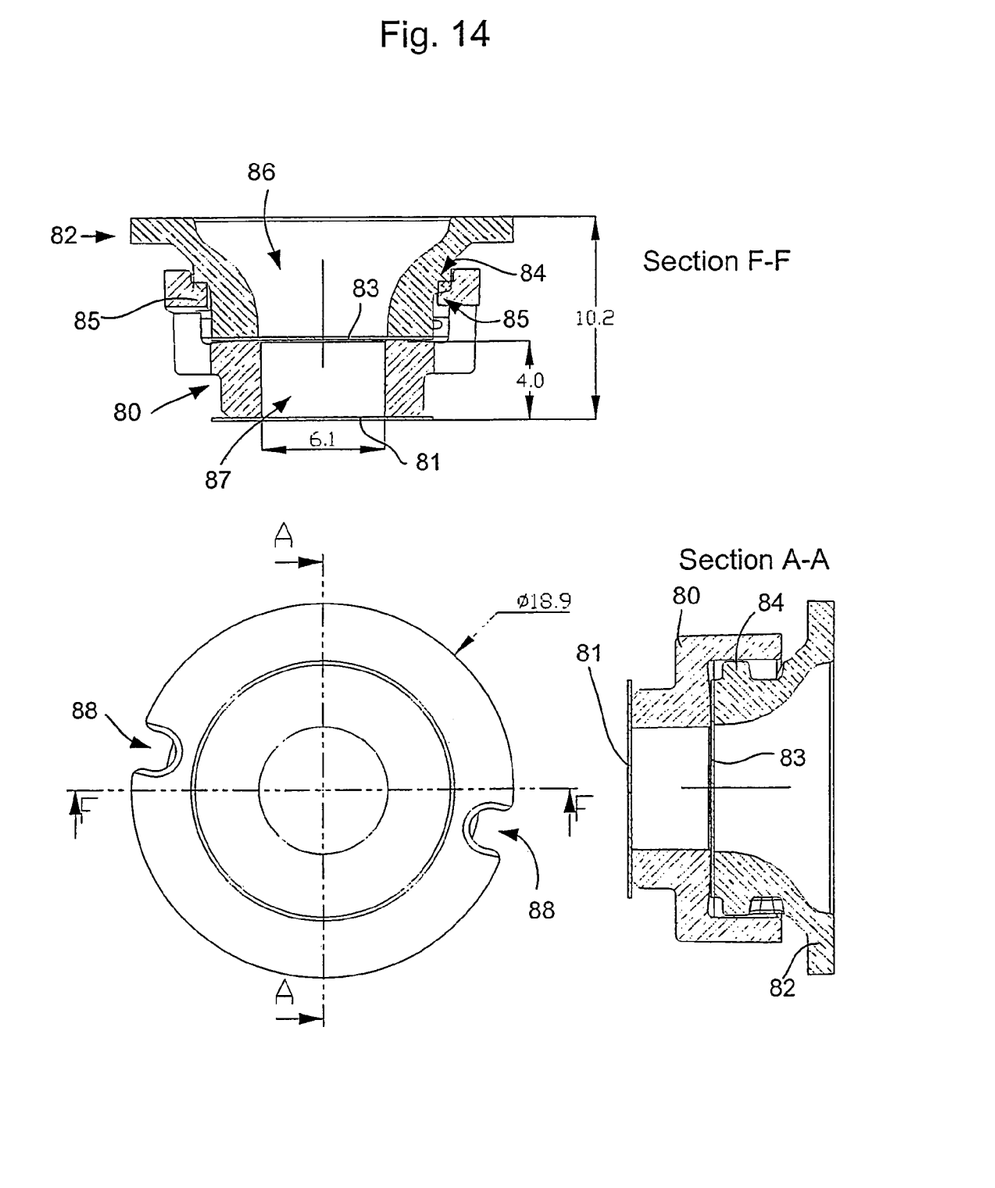
FIG. 14 is a set of three orthographic views of an assembled particle cassette according to a eighth embodiment of the present invention.

To overcome this problem, a particle cassette as shown in the seventh and eighth embodiments of the invention is provided. The particle cassette itself has a built in expansion chamber (120) meaning that the syringe has less components overall. This results in a decrease in manufacturing time and complexity.

The seventh embodiment of the invention is shown in FIG. 13. In this embodiment, the first cassette part (70) has heat sealed to a lower edge a membrane (71). Particles are then located in chamber (77) formed by the inner side walls of the first cassette part (70) and the membrane (71). The second cassette part (72) can then be placed on top of the first cassette part so as to seal off chamber (7.7). As can be seen from FIG. 13, the second cassette part (72) comprises a substantially annular member having a membrane (73) attached (eg. by heat sealing) to its lower edge. The annular second member fits inside part of the annular first member. The second member is locked against the first member by means of ribs (74) on the second member which locate in spaces (75) created between the first and second members during assembly. As can be seen, the ribs (74) have a tapered front edge to aid assembly and are made so as to provide a snug interference fit with the inside annular surface (78) of the first member.

It will also be apparent from FIG. 13 that this embodiment comprises an open chamber (76) that is arranged to open outwardly of the assembled cassette. The chamber (76) lies above (i.e. upstream of) the membrane (73) which separates it from the particle confinement chamber (77). When the cassette is assembled in the finished syringe, the chamber (76) performs the function of the expansion chamber (120) shown in FIG. 15. Please note that FIG. 15 is schematic so that, even though FIG. 15 shows an expansion chamber (120) which diverges in the downstream direction, the expansion chamber provided by chamber (76) of the particle cassette of the seventh embodiment converges in the downstream direction and this results in a needleless syringe which works adequately.

It can be seen that the particle cassette of the seventh embodiment retains the advantages of the previous embodiments in that the particles can be located in chamber (77) and the two cassette parts pressed together to confine the particles in a chamber, without the need to subject the particles to the heating that often accompanies sealing the membranes to the cassette parts. Furthermore, the seventh embodiment integrates part of the needleless syringe, viz, the expansion chamber (120), with the particle cassette, thereby reducing the number of components and the manufacturing time and expense.

An eighth embodiment of the invention is shown in FIG. 14. The eighth embodiment has a construction very similar to that of the seventh embodiment, save for the particular manner in which the first cassette part (80) is connected to the second cassette part (82). Whilst in the seventh embodiment the two parts are pushed together to form an interference fit, the two parts are screwed together in the eighth embodiment by means of threads (84 and 85). A thread (84) is located on the outer surface of the second cassette part (82) and is designed to mate with a corresponding thread (85) located on the inner surface of first cassette part (80).

It will be apparent from both FIGS. 13 and 14 that the first cassette part (70 or 80) contains annular longitudinal protrusions which extend beyond the plane of the upstream membrane (73 or 83) in use. These protrusions allow the first part (70 or 80) to be connected to the respective second part (72 or 82) either by means of an interference fit as shown in FIG. 13, or by means of a screw thread as shown in FIG. 14.

The screw thread is preferably relatively coarse such that the first and second cassette parts can be connected together with relatively few turns. Preferably, less than one turn of relative movement is necessary, more preferably 180° or less of relative rotation. In the most preferred embodiment, a range of movement between 45° and 120°, preferably 90° is sufficient to attach the first and second cassette parts together.

Of course, the various means for attaching the cassette parts shown in the first to seventh embodiments may be combined with the features of the eighth embodiment, for example, seating faces, tapers and detents which provide a "snap-fit" can all be used in combination with the screw thread attachment. Furthermore, a third cassette part may be used in the seventh and eighth embodiments to lock the first and second cassette parts together.

It will be noted from FIG. 14 that two indents (88) are provided on the outer circumferential surface of the second cassette part (82). These indents are designed to receive a tool which assists in applying a torque to the second cassette part (82) when it is screwed to the first cassette part (80). Similar indents may also be provided on the first cassette part (80) if required.

The screw thread design of the eighth embodiment has been found to give a more reproducible face seal between the mating surfaces of the first and second cassette part. This helps to prevents egress of payload from the chamber (87) inside the assembled cassette, and gives a more consistent barrier to potential biological contamination. Furthermore, the integration of the expansion chamber (120) with the particle cassette makes the overall dimensions of the cassette larger than in the prior art which facilitates handling and manipulation during manufacture of the needleless syringe comprising the cassette.

It is envisaged that other embodiments falling within the scope of the present claims can be provided by using combinations of the various attaching methods disclosed in the first to eighth embodiments herein. The type of attaching means to be used depends on the circumstances. For example, there are occasions when a "snap-fit" action is not suitable because the snapping provides a vibrational jolt to the cassette assembly which may damage particularly fragile particles. In such cases, an interference fit or screw fit is preferred.

For each of the embodiments, the materials used to manufacture the cassette parts and the membranes may be conventional, for example, the membranes may be Mylar as disclosed in WO 94/24263 and the first and second cassette parts are preferably manufactured from a plastics material, using injection moulding for example. Both the membranes and cassette parts may be made from polycarbonate such as Evaxone 260 (EVA) polymer. If heat sealing is used, a temperature of 110° C. and pressure of 760 kPa (110 psi) for 1.5 seconds has been found to be acceptable.

The cassette is suitable for any type of particle that one intends to deliver, including powdered drugs (therapeutics, medicaments, vaccines, anaesthetics, analgesics, and the like), diagnostic particles (whether inert or comprising an active ingredient), and carrier particles coated with peptides, proteins or genetic material.

The invention claimed is:

1. A kit of parts for use in the manufacture of a particle cassette for a needleless syringe device, said kit comprising:
    a first cassette part having a first rupturable membrane sealed thereto; and
    a second cassette part having a second rupturable membrane sealed thereto, said first and second cassette parts being arranged to be attachable together so as to create a chamber for the confinement of particles between said first and second membranes, the first and second cassette parts being directly connected to each other,
        wherein one of said first and second cassette parts comprises an open chamber that is arranged to open outwardly with respect to an assembled cassette formed by attaching the first and second cassette parts together when the first and second cassette parts are attached together,
        wherein after the first cassette part and the second cassette part are attached together, they are adapted to be installed in a needleless syringe device which utilizes gas pressure to rupture at least one of the first rupturable membrane and the second rupturable membrane, and
        wherein an inner wall of the second cassette part and an outer wall of the first cassette part define an annular gap around the first cassette part when the first and second cassette parts are directly connected to each other.

2. A kit according to claim 1, wherein said first and second cassette parts are arranged to be attached together by an interference fit.

3. A kit according to claim 1, wherein said first and second cassette parts each comprise corresponding features that provide for a snap fit when said first and second cassette parts are attached together.

4. A kit according to claim 3, wherein said corresponding features comprise a detent and a recess.

5. A kit according to claim 3, wherein said corresponding features are provided on tapered faces which are arranged to contact one another fully when said cassette is properly assembled.

6. A kit according to claim 1, wherein said first and second cassette parts each comprise a seating face which ensures the attainment of a predetermined dimension of said cassette in the direction in which said first and second parts are attachable together.

7. A kit according to claim 1, wherein said first and second cassette parts each comprise a tapered face which are arranged to contact one another fully when said cassette is properly assembled.

8. A kit according to claim 1, further comprising:
    a third cassette part for locking together said first and second cassette parts.

9. A kit according to claim 8, wherein said third cassette part has a third membrane sealed thereto.

10. A kit according to claim 8, wherein said third cassette part comprises a protrusion for creating an interference fit with said second cassette part.

11. A kit according to claim 8, wherein said first and second cassette parts are shaped so as to be fitted together leaving an annular gap around said first cassette part, and wherein said third cassette part has a portion that inserts into said annular gap so as to lock said first, second and third cassette parts together.

12. A kit according to claim 8, wherein said third cassette part comprises gas ports for supplying gas to an annular space around said first cassette part.

13. A kit according to claim 1, wherein said first and second cassette parts are shaped so as to be fitted together leaving an annular gap around said first cassette part.

14. A kit according to claim 1, wherein said first cassette part comprises at least one transfer duct for supplying gas to said particle confinement chamber.

15. A kit according to claim 1, wherein said first and second cassette parts are arranged to be attached by a screw thread.

16. A kit according to claim 15, wherein said screw thread is coarse such that the first and second cassette parts can be attached together by a relative rotation of 180° or less.

17. A kit according to claim 1, wherein said first and second cassette parts are arranged to be attached together by a method other than heat sealing.

18. A kit according to claim 17, wherein the second cassette part is adapted to fit concentrically inside the first cassette part, the second cassette part comprising a male part and the first cassette part comprising a corresponding female part.

19. A particle cassette for a needleless syringe comprising: an assembled kit of the parts claimed in claim 1; and particles provided in said chamber between said first and second membranes.

20. A particle cassette according to claim 19, wherein said particles comprise powdered drug.

21. A device comprising: a needleless syringe including the particle cassette of claim 19.

22. A kit according to claim 1, wherein the second cassette part is adapted to fit concentrically inside the first cassette part, the second cassette part comprising a male part and the first cassette part comprising a corresponding female part.

23. A kit according to claim 1, wherein said first cassette part is substantially annular and defines a receptacle for receiving particles.

24. A kit according to claim 23, wherein said second cassette part is substantially annular and is attachable concentrically around or inside said first cassette part.

25. A kit according to claim 1, wherein at least one of the first and second cassette parts form an entirety of a sidewall of the chamber for the containment of particles.

26. A kit according to claim 1, wherein the first and second cassette parts together form an entirety of a sidewall of the chamber for the containment of particles.

27. A kit according to claim 1, wherein the first and second rupturable membranes are consecutively arranged without an intervening membrane to form upper and lower surfaces of the chamber for the confinement of particles.

28. A method of assembling a particle cassette for a needleless syringe device, said method comprising:

(a) sealing a first rupturable membrane to a first cassette part;

(b) sealing a second rupturable membrane to a second cassette part (c) supplying articles to said first cassette part; and (d) attaching said first and second cassette parts together so that the first and second cassette parts are directly connected to each other so as to create a chamber confining said supplied particles between said first and second membranes, wherein any step according to step (a) is carried out before step (c), and wherein after steps (a) through (d) are executed, the first cassette part and the second cassette part are adapted to be installed in a needleless syringe device which utilizes gas pressure to rupture at least one of the first rupturable membrane and the second rupturable membrane, and wherein an inner wall of the second cassette part and an outer wall of the first cassette part define an annular gap around the first cassette part when the first and second cassette parts are directly connected to each other.

29. A method according to claim 28, wherein said sealing steps (a) and (b) comprise heat sealing.

30. A method according to claim 28, wherein attaching step (d) does not involve the application of heat.

31. A method according to claim 28, wherein attaching step (d) is carried out at the same temperature as supplying step (c).

32. A method according to claim 28, wherein said first cassette part is substantially annular and defines a receptacle, and wherein said particles are supplied to said receptacle in step (c).

33. A method according to claim 28, wherein said second cassette part is substantially annular, and wherein step (d) comprises fitting said second cassette part concentrically around or inside said first cassette part.

34. A method according to claim 28, wherein step (d) comprises establishing an interference fit between said first and second cassette parts.

35. A method according to claim 28, wherein said first and second cassette parts each comprise corresponding features that provide for a snap fit when said first and second cassette parts are attached, and wherein step (d) comprises associating said corresponding features to snap said second cassette part onto said first cassette part.

36. A method according to claim 35, wherein said corresponding features comprise a detent and a recess, and wherein step (d) comprises locating said detent in said recess.

37. A method according to claim 28, wherein sealing steps (a) and (b) comprise sealing said first and second membranes around their periphery to the substantially annular first and second cassette parts, respectively.

38. A method according to claim 28, wherein step (c) is carried out before step (b).

39. A method according to claim 28, wherein said first and second cassette parts each comprise a seating face substantially perpendicular to the direction in which the parts are moved to be attached, and wherein step (d) comprises the contacting of said respective seating faces.

40. A method according to claim 28, wherein said first and second cassette parts each comprise a tapered face at an acute angle to the direction in which the parts are moved to be attached, and wherein step (d) comprises the contacting of said respective tapered faces.

41. A method according to claim 28, wherein said attaching step (d) comprises introducing a third cassette part so as to attach said first and second cassette parts together.

42. A method according to claim 41, further comprising: (e) sealing a third rupturable membrane to said third cassette part before employing said third cassette part.

43. A method according to claim 28, wherein step (d) comprises rotating the first and second cassette parts relative to one another so as to screw them together.

44. A method according to claim 43, wherein said relative rotation is less than 180°.

45. A particle cassette for a needleless syringe device, produced using the assembly method of claim 28.

46. A method according to claim 28, wherein the chamber is formed by the first cassette part directly contacting the second cassette part.

47. A method according to claim 28, wherein the step of attaching the first and second cassette parts together includes inserting the second cassette part into the first cassette part so that the second cassette part comprises a male part and the first cassette part comprises a female cassette part.

48. A method according to claim 28, wherein the first and second rupturable membranes are consecutively arranged without an intervening membrane to form upper and lower surfaces of the chamber for confining said particles.

49. A kit for use in the manufacture of a particle cassette for a needleless syringe device, said kit comprising:
a first cassette part having a first rupturable membrane sealed thereto;
a second cassette part having a second rupturable membrane sealed thereto, said first and second cassette parts being arranged to be attachable together so as to create a chamber for the confinement of particles between said first and second membranes, the first and second cassette parts being directly connected to each other; and
a third cassette part for locking together said first and second cassette parts,
wherein the cassette parts are adapted to, after the first cassette part and the second cassette part are attached together and locked together by the third cassette part, be installed in a needleless syringe device which utilizes gas pressure to rupture at least one of the first rupturable membrane and the second rupturable membrane, and
wherein an inner wall of the second cassette part and an outer wall of the first cassette part define an annular gap around the first cassette part when the first and second cassette parts are directly connected to each other.

50. A kit according to claim 49, wherein the first and second rupturable membranes are consecutively arranged without an intervening membrane to form upper and lower surfaces of the chamber for the confinement of particles.

51. A kit of parts for use in the manufacture of a particle cassette for a needleless syringe device, said kit comprising:
a first cassette part having a first rupturable membrane sealed thereto; and
a second cassette part having a second rupturable membrane sealed thereto, said first and second cassette parts being arranged to be attachable together so as to create a chamber for the confinement of particles between said first and second membranes, the first and second cassette parts being directly connected to each other,
wherein said first and second cassette parts are shaped so as to be fitted together leaving an annular gap around said first cassette part,
wherein the cassette parts are adapted to, after the first cassette part and the second cassette part are attached together, be installed in a needleless syringe device which utilizes gas pressure to rupture at least one of the first rupturable membrane and the second rupturable membrane, and
wherein an inner wall of the second cassette part and an outer wall of the first cassette part define an annular gap around the first cassette part when the first and second cassette parts are directly connected to each other.

52. A kit according to claim 51, wherein the first and second rupturable membranes are consecutively arranged without an intervening membrane to form upper and lower surfaces of the chamber for the confinement of particles.

* * * * *